US006780441B2

(12) United States Patent
Solanki

(10) Patent No.: US 6,780,441 B2
(45) Date of Patent: Aug. 24, 2004

(54) COMPOSITION OF ELEVEN HERBALS FOR TREATING CANCER

(75) Inventor: Ranjitsinh Solanki, Gujarat (IN)

(73) Assignee: Sahajanand Biotech Private Limited, Gujarat (IN)

( * ) Notice: Subject to any disclaimer, the term of this patent is extended or adjusted under 35 U.S.C. 154(b) by 0 days.

(21) Appl. No.: 10/257,083

(22) PCT Filed: Jul. 10, 2002

(86) PCT No.: PCT/IB02/02698

§ 371 (c)(1),
(2), (4) Date: Oct. 8, 2002

(87) PCT Pub. No.: WO03/006036

PCT Pub. Date: Jan. 23, 2003

(65) Prior Publication Data

US 2004/0009240 A1 Jan. 15, 2004

(30) Foreign Application Priority Data

Jul. 11, 2001 (GB) .............................................. 0116948

(51) Int. Cl.$^7$ .............................................. A61K 35/78
(52) U.S. Cl. ...................................................... 424/725
(58) Field of Search ........................................ 424/725

(56) References Cited

FOREIGN PATENT DOCUMENTS

| JP | 7304685 | 11/1995 |
| WO | 9108750 | 6/1991 |
| WO | 9418993 | 9/1994 |

OTHER PUBLICATIONS

De Silva et al., "A New Sesqui Terpene Lactone From Elephantopus–Scaber," 1982 Phytochemistry (Oxford) vol. 21, No. 5, pp. 1173–1175.
Al–Hindawi et al., "Anti–Inflammatory Activity of Some Iraqi Plants Using Intact Rats,"1989 Journal of Ethnopharmacology, Elsevier Scientific Publishers Ltd., IE, vol. 26, No. 2, pp. 163–168.
Database WPI, Section Ch. Week 199604, 1996 Derwent Publications Ltd., London GB.

Sohn et al., "Activity of a crude extract formulation in experimental hepatic amoebiasis and in immunomodulation studies," 1996, Journal of Ethnopharmacology, vol. 54, No. 2–3, pp. 119–124.
Kapil et al., "Immunopotentiating compounds from *Tinospora cordifoia*," 1997 Journal of Ethnopharmacology, Elsevier Scientific Publishers Ltd., IE, pp. 89–95.
Menon et al., "Effect of rasayanas in the inhibition of lung metastasis induced by B16f–10 melanoma cells," Dec. 1997, Journal of Experimental & Clinical Cancer Research, vol. 16, No. 4, pp. 365–368.
Jagetia et al., "Evaluation of the antineoplastic activity of guduchi (*Tinospora cordifolia*) in cultured HeLa cells" 1998, Cancer Letters, vol. 127, pp. 71–82.
Praveen et al., "Effect of "Rasayanas" a herbal drug preparation on cell–mediated Immune responses in tumour bearing mice," Jan. 1999, Indian Journal of Experimental Biology, vol. 37, No. 1, pp. 23–26.
Tsai et al., "Anti–inflammatory effects of Taiwan folk medicine 'Teng–Khia–U' on carrageenan–and adjuvant–Induced paw edema in rats,", Jan. 1999, Journal of Ethnopharmacology, vol. 64, No. 1, pp. 85–89.
Leemol et al., "Effect of *Withania somnifera* on cytokine production in normal and cyclophosphamide mice," Nov. 1999, Immunopharmacology and Immunotoxicology, vol. 21, No. 4, pp. 695–703.
Mandal et al., "Anti–inflammatory evaluation of *Ficus racemosa* Linn. leaf extract." Sep. 2000, Journal of Ethnopharmacology, Ireland, Sep. 2000, vol. 72, No. 1–2 pp. 87–92.

Primary Examiner—Christopher R. Tate
(74) Attorney, Agent, or Firm—Volpe and Koenig, P.C.

(57) ABSTRACT

A pharmaceutical or medicinal preparation which comprises a mixture of the following eleven herbs: *Withania somnifera, Chlorphyton borivilianum, Boerhavia diffusa, Elephantopus scaber, Moringa oleifera, Tecoma undulata, Bauhinia purpurea, Ficus racemosa, Cyperus rotundus, Sphaeranthus acmella* and *Tinospora cordifolia*; or a mixture of the active ingredients that have been extracted from those herbs or chemically synthesised. The herbal formulation of the invention is effective for the treatment of cancer, in particular squamous cell carcinomas, tumours and other metastatic states, including lung cancer.

18 Claims, No Drawings

COMPOSITION OF ELEVEN HERBALS FOR TREATING CANCER

TECHNICAL FIELD

This invention relates to a new herbal formulation which has been found to be effective for the treatment of cancer. More particularly, the formulation can be used to treat squamous cell carcinomas, tumours and other metastatic states, including lung cancer.

The conventional treatment of tumerous cancers, including lung cancer, comprises surgery, chemotherapy and/or radiotherapy. The drugs given during chemotherapy are of necessity very powerful and, in consequence, can have serious and undesirable side-effects. There is therefore a need for improved pharmaceutical or medicinal preparations for use in the treatment of cancer. It is the object of this invention to provide such a product.

According to this invention there is provided a pharmaceutical or medicinal preparation which comprises a mixture of the following eleven herbs: *Withania somnifera, Chlorphyton borivilianum, Boerhavia diffusa, Elephantopus scaber, Moringa oleifera, Tecoma undulata, Bauhinia purpurea, Ficus racemosa, Cyperus rotundus, Sphaeranthus acmella* and *Tinospora cordifolia* or a mixture of the active ingredients that have been extracted from those herbs or chemically synthesized. This product has been found by the inventor to be particularly effective for the treatment of lung cancer, including all types of bronchogenic carcinomas and pleural malignancies. The preparation is preferably formulated for administration to patients as a liquid or syrup, but could also be administered as a capsule or tablet.

The ingredients for a typical herbal formulation according to this invention are set out in Table I. It should be appreciated that the proportions of the individual herbs may be varied and the figures quoted in Table I are by way of illustration only. In particular, the proportions of one or more of the components may be varied in order to optimize the pharmacological effects produced by the formulation to suit the specific needs of patients being treated.

It is an important feature of the product of the present invention that it contains a mixture of herbs, or extracts from herbs, rather than being based on a single herb. A synergistic effect has been noticed between the various ingredients. The herbs when exhibited unexpected synergistic property. The activities of similar herbs are combined to optimize and enhance the pharmacological effects without increasing the adverse toxic reactions (which becomes a distinct possibility if the herbs are used singly in a concentration of 100%). The advantage of a multi-drug regimen also lies in the fact that the possibility of development of drug resistance is minimized.

Preliminary clinical trials of the product of this invention have produced definite clinical evidence of improvement in the condition of patients suffering from lung cancer. These improvements include:

i) reduction in the tumour size as noted on X-ray, ultra sonography, C.T. Scan and MRI.
ii) improvement in the relevant biochemical parameters; and
iii) disappearance of malignant cells from sputum and pleural fluid;

and more subjectively:

i) sense of well being,
ii) improvement in appetite, and
iii) increased vigour and enthusiasm in daily activities.

The formulation of this invention is itself effective for the treatment of cancer. It may also be used as an adjuvant to conventional modes of anticancer therapy, namely radiotherapy and/or chemotherapy. The formulation may be presented as a dietary supplement for patients diagnosed as having any type of cancer. It may also be used to create a sense of general well being and to increase the vitality in patients diagnosed as having any type of cancer, to increase the appetite, restore health and increase the lifespan of patients diagnosed as having any type of cancer; to improve the ambulatory capacity in patients diagnosed as having any type of cancer; to activate the nervous system, prevent degenerative changes, stimulate regeneration and improve the psychological status in patients diagnosed as having any type of cancer, and to stimulate metabolism, accelerate anabolism, promote catabolism thereby flushing the body of toxic metabolites and reducing the side effects of chemotherapy and radiotherapy. The hepatic clearance of substances like iron and ferritin in cases of thalassemia is also improved, thereby reducing the iron overload in such cases.

The manufacture of a product according to the present invention will now be illustrated by the following example. However, it will be appreciated that the active ingredients may be chemically synthesised as an alternative to being extracted from the natural herbs.

EXAMPLE

Method of Extraction

Each of the herbal components of the formulation were de-seeded (wherever required), ground finely to powder form and then submitted individually to conventional solvent extraction methods.

By way of illustration only, the extraction can be performed by using volatile freon gas. This process has the advantage of being fast and also has the ability to preserve the active chemicals (alkaloids, non-alkaloids, electrolytes, minerals, etc.) in their natural form (as it does not involve heating and denaturation at any stage of the process). Freon, being a highly volatile compound with its boiling point at $-21°$ C., evaporates totally after extraction, yielding an ultrapure concentrate of the chemicals. The chemicals are thereafter diluted appropriately and mixed in the proportions mentioned in Table 1.

Preliminary Clinical Data

Case 1

A 53 year old male patient had complaints of chest pain and blood in sputum. Bronchoscopic biopsy revealed a squamous cell carcinoma of the lung. The patient refused conventional therapy and was put on the herbal formulation of the present invention. Two gelatin capsules containing 450 mg to 480 mg each of the powdered herbal formulation was administered to the patient once every 8 hours, three times a day. One month after therapy began, there was a complete stoppage of haemoptysis and chest pain with improvement in appetite and ambulatory capacity.

Case 2

A male patient 42 years old and a habitual smoker was diagnosed as a stage III squamous cell carcinoma of lung with hepatic metastasis. The patient refused conventional therapy and was put on the herbal formulation of the present invention. Two gelatin capsules containing 450 mg to 480 mg each of the powdered herbal formulation was administered to the patient once every 8 hours, three times a day. The tumour size after six months of herbal therapy was the same as at the time of diagnosis. However, there has been a marked improvement in the psychological status of the patient and also in his appetite and ambulatory capacity.

It can be concluded that the herbal formulation of the present invention has a very beneficial effect on apparently terminally ill patients suffering from malignant tumours and even metastatic carcinomas. Furthermore, therapy with this formulation appears to have the advantages of targeting only malignant cells, producing no serious adverse side effects, causing no damage to healthy cells, improving the immunomodulatory effect and also producing an anti-oxidant effect.

TABLE 1

Polyherbal formulation for All Cancers
Description of Ingredients

| Sr. No. | Latin Binomial | Common Names | Distribution | Parts used | Quantity | Adverse Reactions |
|---|---|---|---|---|---|---|
| 1. | Withania somnifera | Ashwagandha | All parts of India | Roots, leaves | 8–12% preferably 10% | None |
| 2. | Chlorophyton borivilianum | Shwet Mushali | Cultivated throughout India | Roots | 3–8% preferably 5% | None |
| 3. | Boerhavia diffusa | Punarnava mool | Cultivated throughout India | Rhizomes (dried as well as raw) | 8–12% preferably 10% | None |
| 4. | Elephantopus scaber | Gaozaban | Few parts of India | Roots, stem | 3–8% preferably 5% | None |
| 5. | Moringa oleifera | Saragavo | Throughout India along roadsides and waste places | Seeds, Leaves | 8–12% preferably 10% | None |
| 6. | Tecoma undulata | Ragat rohida | Cultivated throughout India | Stem | 8–12% preferably 10% | None |
| 7. | Bauhinia purpurea | Kanchnar | Cultivated throughout India | Stem | 8–12% preferably 10% | None |
| 8. | Ficus racemosa | Udumbar | Throughout India | Stem | 3–8% preferably 5% | None |
| 9. | Cyperus rotundus | Nagarmoth | Throughout India | Rhizomes | 8–12% preferably 10% | None |
| 10. | Sphaeranthus acmella | Gorakhmundi | Throughout India | Whole plant | 3–8% preferably 5% | None |
| 11. | Tinospora cordifolia | Tinospora | Throughout India in forests | Stem | 17–23% preferably 20% | None |

What is claimed is:

1. A pharmaceutical or medicinal preparation for treating cancer comprising an effective amount of a mixture of extracts obtained from the herbs *Withania somnifera, Chlorophyton borivilianum, Boerhavia diffusa, Elephantopus scaber, Moringa oleifera, Tecoma undulata, Bauhinia purpurea, Ficus racemosa, Cyperus rotundus, Sphaeranthus acmella* and *Tinospora cordifolia*.

2. A pharmaceutical or medicinal preparation as claimed in claim 1, for use in the treatment of squamous cell carcinomas, tumours and metastatic cancers.

3. A pharmaceutical or medicinal preparation as claimed in claim 1, for use in the treatment of lung cancer.

4. A pharmaceutical or medicinal preparation as claimed in claim 1, for use as a cancer immunomodulator, general immunomodulator and anti-inflammatory agent.

5. A pharmaceutical or medicinal preparation as claimed in claim 1, for use as an adjuvant to radiotherapy.

6. A pharmaceutical or medicinal preparation as claimed in claim 1, wherein the percentages by weight of herbs is as follows:

| | |
|---|---|
| Withania somnifera | 8–12% |
| Chlorophyton borivilianum | 3–8% |
| Boerhavia diffusa | 8–12% |
| Elephantopus scaber | 3–8% |
| Moringa oleifera | 8–12% |

-continued

| | |
|---|---|
| Tecoma undulata | 8–12% |
| Bauhinia purpurea | 8–12% |
| Ficus racemosa | 3–8% |
| Cyperus rotundus | 8–12% |
| Sphaeranthus acmella | 3–8% |
| Tinospora cordifolia | 17–23%. |

7. A pharmaceutical or medicinal preparation as claimed in claim 6, wherein the percentages by weight of herbs is as follows:

| | |
|---|---|
| Withania somnifera | 10% |
| Chlorophyton borivilianum | 5% |
| Boerhavia diffusa | 10% |
| Elephantopus scaber | 5% |
| Moringa oleifera | 10% |
| Tecoma undulata | 10% |

-continued

| | |
|---|---|
| Bauhinia purpurea | 10% |
| Ficus racemosa | 5% |
| Cyperus rotundus | 10% |
| Sphaeranthus acmella | 5% |
| Tinospora cordifolia | 20%. |

8. A dietary supplement for patients diagnosed as having cancer, wherein the dietary supplement comprises an effective amount of the pharmaceutical or medicinal preparation as claimed in claim 1.

9. A pharmaceutical or medicinal preparation as claimed in claim 1, for use as an adjuvant to chemotherapy.

10. A pharmaceutical or medicinal preparation for treating cancer comprising an effective amount of a mixture of extracts obtained from the herbs *Withania somnifera, Chlorophyton borivilianum, Boerhavia diffusa, Elephantopus scaber, Moringa oleifera, Tecoma undulata, Bauhinia purpurea, Ficus racemosa, Cyperus rotundus, Sphaeranthus acmella* and *Tinospora cordifolia*, whereby the extracts are obtained using freon gas.

11. A pharmaceutical or medicinal preparation as claimed in claim 10, for use in the treatment of squamous cell carcinomas, tumours and metastatic cancers.

12. A pharmaceutical or medicinal preparation as claimed in claim 10, for use in the treatment of lung cancer.

13. A pharmaceutical or medicinal preparation as claimed in claim 10, for use as a cancer immunomodulator, general immunomodulator and anti-inflammatory agent.

14. A pharmaceutical or medicinal preparation as claimed in claim 10, for use as an adjuvant to radiotherapy.

15. A pharmaceutical or medicinal preparation as claimed in claim 10, wherein the percentages by weight of herbs is as follows:

| | |
|---|---|
| Withania somnifera | 8–12% |
| Chlorophyton borivilianum | 3–8% |
| Boerhavia diffusa | 8–12% |
| Elephantopus scaber | 3–8% |
| Moringa oleifera | 8–12% |
| Tecoma undulata | 8–12% |
| Bauhinia purpurea | 8–12% |
| Ficus racemosa | 3–8% |
| Cyperus rotundus | 8–12% |
| Sphaeranthus acmella | 3–8% |
| Tinospora cordifolia | 17–23%. |

16. A pharmaceutical or medicinal preparation as claimed in claim 15, wherein the percentages by weight of herbs is as follows:

| | |
|---|---|
| Withania somnifera | 10% |
| Chlorophyton borivilianum | 5% |
| Boerhavia diffusa | 10% |
| Elephantopus scaber | 5% |
| Moringa oleifera | 10% |
| Tecoma undulata | 10% |
| Bauhinia purpurea | 10% |
| Ficus racemosa | 5% |
| Cyperus rotundus | 10% |
| Sphaeranthus acmella | 5% |
| Tinospora cordifolia | 20%. |

17. A dietary supplement for patients diagnosed as having cancer, wherein the dietary supplement comprises an effective amount of the pharmaceutical or medicinal preparation as claimed in claim 10.

18. A pharmaceutical or medicinal preparation as claimed in claim 10, for use as an adjuvant to chemotherapy.

\* \* \* \* \*